(12) United States Patent
Yoshida et al.

(10) Patent No.: US 10,342,808 B2
(45) Date of Patent: Jul. 9, 2019

(54) ROCURONIUM BROMIDE INJECTION SOLUTION-FILLED PREFILLED SYRINGE

(71) Applicant: Terumo Kabushiki Kaisha, Shibuya-ku, Tokyo (JP)

(72) Inventors: Akira Yoshida, Sukagawa (JP); Yuki Watanabe, Fukushima (JP); Aiko Horiuchi, Hadano (JP); Hiroki Yoshikawa, Hadano (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 0 days.

(21) Appl. No.: 15/279,924

(22) Filed: Sep. 29, 2016

(65) Prior Publication Data

US 2017/0014431 A1    Jan. 19, 2017

Related U.S. Application Data

(63) Continuation of application No. PCT/JP2015/058994, filed on Mar. 24, 2015.

(30) Foreign Application Priority Data

Mar. 31, 2014    (JP) ................................ 2014-073579

(51) Int. Cl.
| | |
|---|---|
| A61K 31/58 | (2006.01) |
| A61K 9/00 | (2006.01) |
| A61L 31/02 | (2006.01) |
| A61L 31/04 | (2006.01) |
| A61M 5/31 | (2006.01) |
| A61M 5/315 | (2006.01) |
| A61M 5/28 | (2006.01) |

(52) U.S. Cl.
CPC ............ *A61K 31/58* (2013.01); *A61K 9/0019* (2013.01); *A61L 31/028* (2013.01); *A61L 31/048* (2013.01); *A61L 31/049* (2013.01); *A61M 5/3129* (2013.01); *A61M 5/31511* (2013.01); *A61M 5/31513* (2013.01); *A61M 5/28* (2013.01); *A61M 2005/3104* (2013.01); *A61M 2005/3131* (2013.01)

(58) Field of Classification Search
CPC ..... A61K 31/58; A61K 9/0019; A61L 31/028; A61L 31/048; A61L 31/049; A61M 5/3129; A61M 5/31511; A61M 5/31513; A61M 2005/3104; A61M 2005/3131; A61M 5/28
See application file for complete search history.

(56) References Cited

U.S. PATENT DOCUMENTS

| | | | | |
|---|---|---|---|---|
| 8,183,316 B2* | 5/2012 | Goodman | ............ | B60C 1/0016 152/151 |
| 2003/0100696 A1 | 5/2003 | Muraki | | |
| 2007/0053788 A1 | 3/2007 | Zhao | | |
| 2010/0249296 A1 | 9/2010 | Kimura et al. | | |
| 2012/0184920 A1 | 7/2012 | Okihara et al. | | |
| 2012/0266871 A1 | 10/2012 | Ohbi | | |
| 2013/0041241 A1* | 2/2013 | Felts | ..................... | C23C 16/045 600/364 |
| 2015/0021339 A1 | 1/2015 | Felts et al. | | |
| 2016/0022912 A1 | 1/2016 | Hernandez | | |

FOREIGN PATENT DOCUMENTS

| | | |
|---|---|---|
| CN | 102858393 A | 1/2013 |
| EP | 2 554 202 A1 | 2/2013 |
| JP | 2000-342688 A | 12/2000 |
| JP | 2002-301133 A | 10/2002 |
| JP | 2011-067362 A | 4/2011 |
| JP | 2013-203675 A | 10/2013 |
| WO | WO 2011/040522 A1 | 4/2011 |
| WO | 2011/122393 A1 | 10/2011 |
| WO | WO 2013/071138 A1 | 5/2013 |
| WO | WO 2013/116353 A1 | 8/2013 |

OTHER PUBLICATIONS

International Search Report (PCT/ISA/210) dated Apr. 8, 2015, by the Japanese Patent Office as the International Searching Authority for International Application No. PCT/JP2015/058994.

Written Opinion (PCT/ISA/237) dated Apr. 8, 2015, by the Japanese Patent Office as the International Searching Authority for International Application No. PCT/JP2015/058994.

English language translation of International Preliminary Report on Patentability and Written Opinion of the International Searching Authority (Forms PCT/IB/338, PCT/IB/373 and PCT/ISA/237) dated Oct. 13, 2016, by the International Bureau of WIPO, in corresponding International Application No. PCT/JP2015/058994. (9 pages).

Office Action (Notification of Reasons for Refusal) dated Sep. 12, 2017, by the Japanese Patent Office in corresponding Japanese Patent Application No. 2014-073579, and an English Translation of the Office Action. (6 pages).

(Continued)

*Primary Examiner* — Irina S Zemel
*Assistant Examiner* — Jeffrey S Lenihan
(74) *Attorney, Agent, or Firm* — Buchanan Ingersoll & Rooney PC

(57) ABSTRACT

A rocuronium bromide injection solution-prefilled syringe of the present invention includes a syringe comprising an outer cylinder made of synthetic resin, a gasket which is accommodated inside the outer cylinder and liquid-tightly slidable inside the outer cylinder, and a seal member for sealing a distal end opening of the outer cylinder; and a rocuronium bromide injection solution filled inside the syringe. The gasket is formed by vulcanized chlorinated butyl rubber added calcined clay, and said calcined clay is only added as an inorganic filler classified as an inorganic reinforcing agent and an inorganic filling agent.

8 Claims, 3 Drawing Sheets

(56) References Cited

OTHER PUBLICATIONS

Extended European Search Report issued by the European Patent Office dated Nov. 2, 2017 in corresponding European Application No. 15772563.1 (7 pages).
Search Report dated Jan. 17, 2019, by the State Intellectual Property Office of People's Republic of China in corresponding Chinese Patent Application 201580016699.3 . (2 pages).
Office Action (The First Office Action) dated Jan. 29, 2019, by the State Intellectual Property Office of People's Republic of China in corresponding Chinese Patent Application 201580016699.3 and an English Translation of the Office Action. (11 pages).

* cited by examiner

ROCURONIUM BROMIDE INJECTION SOLUTION-FILLED PREFILLED SYRINGE

TECHNICAL FIELD

The present invention relates to a prefilled syringe, made of synthetic resin, in which a rocuronium bromide injection solution is filled.

BACKGROUND ART

As a prefilled syringe in which an injection solution is filled, many proposals have been made. The present applicant proposed such a prefilled syringe as disclosed in the specification of Japanese Patent Application Laid-Open Publication No. 2013-203675 (patent document 1).

The dexmedetomidine used in the invention of the patent document 1 is a compound, having a sedative action, which is a central α2-adrenergic receptor agonist being strong and having a high selectivity.

As an injection formulation, a rocuronium bromide injection formulation is known. The rocuronium bromide is a compound which acts as an antagonist against a nicotinic acetylcholine receptor present in the postsynaptic membrane of neuromuscular junctions and thus has a nondepolarizing muscle relaxation action of antagonizing the transmission of acetylcholine-caused excitement from nerves to muscles.

A rocuronium bromide injection formulation is used to relax muscles at an anesthetic administering time and a tracheal intubation time. Thus the rocuronium bromide injection solution is a formulation having a high possibility of being used at an emergent administration time. The rocuronium bromide injection formulation is a vial formulation to be administered intravenously or continuously. Thus workloads including the transfer of a liquid medicine to a syringe barrel have become a problem in medical fronts. Thus there is a strong demand for the improvement of the formulation from the medical front.

A prefilled syringe in which a liquid medicine is filled in advance has been conventionally used to prevent medicines from being mixed up, prevent nosocomial infection, improve disposability, and increase the efficiency of hospital service. As the material for the prefilled syringe, glass and various plastics have been used. Because the prefilled syringe made of synthetic resin is lighter and more resistant to breakage than the prefilled syringe made of glass, the use of the prefilled syringe made of the synthetic resin allows dispensing works to be performed more safely than the prefilled syringe made of glass in the medical front.

From the above-described standpoint, it is preferable to use the rocuronium bromide injection solution for the formulation to be filled in the prefilled syringe made of synthetic resin. But there is a case in which a medicine has interaction with an outer cylinder of the syringe or a gasket made of rubber. Thus it is conventionally necessary to investigate the use of the rocuronium bromide injection solution for the prefilled syringe. Because the rocuronium bromide contained in the rocuronium bromide injection solution as its main component is stable in an aqueous solution whose pH is about four, the rocuronium bromide is formulated under an acidic condition.

PRIOR ART DOCUMENTS

Patent Documents

Patent document 1: Japanese Patent Application Laid-Open Publication No. 2013-203675

SUMMARY OF THE INVENTION

Problems to be Solved by the Invention

As described above, because the rocuronium bromide contained in the rocuronium bromide injection solution as its main component is stable in the aqueous solution whose pH is about four, the rocuronium bromide is prepared under the acidic condition. In a case where the rocuronium bromide injection solution is exposed to the acidic condition for a long time, there is a possibility that the gasket made of rubber may be deformed or be denatured. To overcome this problem, the present inventors have made energetic researches on the deformation of the gasket made of rubber when the syringe made of synthetic resin in which the rocuronium bromide injection solution has been filled is preserved for a long time. As a result, unexpectedly, they have found that by using a specific inorganic filler, the rocuronium bromide injection solution-filled prefilled syringe can be stably preserved for a long time without deformation of a gasket.

It is an object of the present invention to provide a rocuronium bromide injection solution-filled prefilled syringe in which a gasket is not deformed or denatured and the rocuronium bromide injection solution can be preserved for a long time in a stable status.

Means for Solving the Problems

The means for achieving the above-described object is as described below.

A rocuronium bromide injection solution-prefilled syringe of the present invention includes a syringe comprising an outer cylinder made of synthetic resin, a gasket which is accommodated inside the outer cylinder and liquid-tightly slidable inside the outer cylinder, and a seal member for sealing a distal end opening of the outer cylinder; and a rocuronium bromide injection solution filled inside the syringe. The gasket is formed by vulcanized chlorinated butyl rubber added calcined clay, and said calcined clay is only added as an inorganic filler classified as an inorganic reinforcing agent and an inorganic filling agent.

MODE FOR CARRYING OUT THE INVENTION

Figure 1:
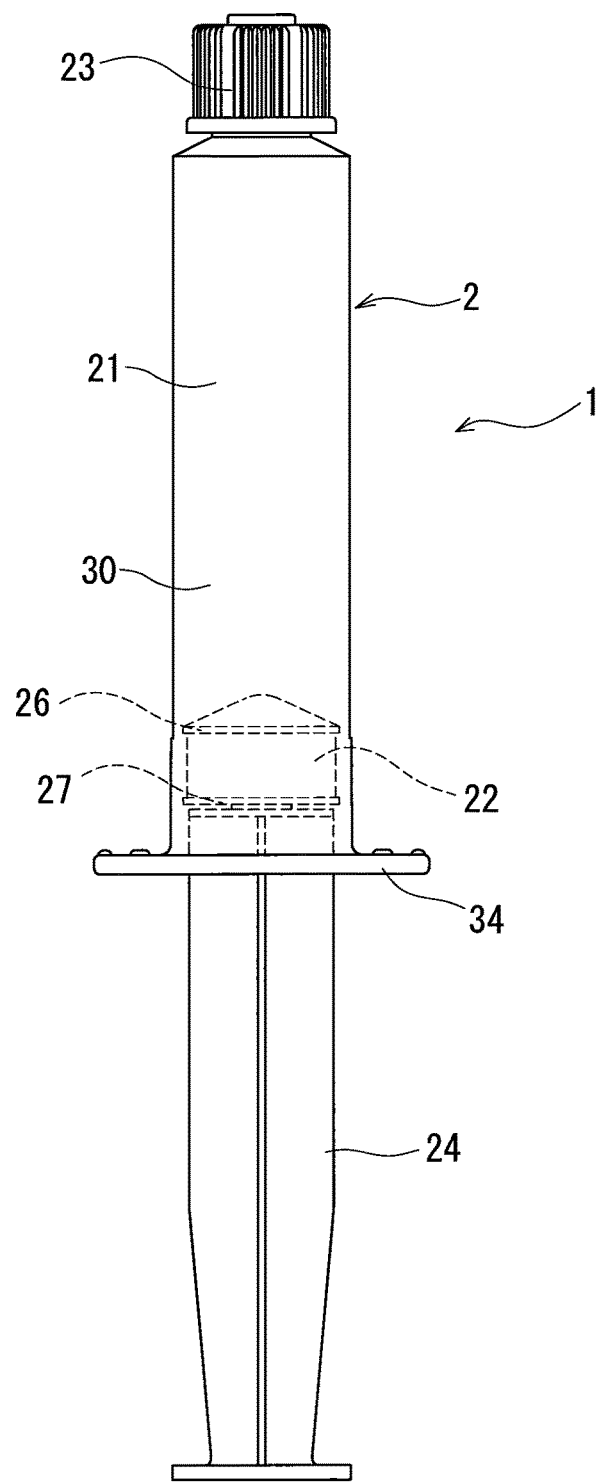
FIG. 1 is a front view of an embodiment of a rocuronium bromide injection solution-filled prefilled syringe of the present invention.

The rocuronium bromide injection solution-prefilled syringe of the present invention is described below with reference to embodiments.

A rocuronium bromide injection solution-prefilled syringe 1 of the present invention is constructed of a syringe 2 comprising an outer cylinder 21 made of synthetic resin, a gasket 22 which is accommodated inside the outer cylinder 21 and liquid-tightly slidable inside the outer cylinder, and a seal member 23 for sealing a distal end opening of the outer cylinder 21; and a rocuronium bromide injection solution 3 filled inside the syringe 2. The gasket 22 is formed by vulcanized chlorinated butyl rubber added calcined clay, and calcined clay is only added as an inorganic filler classified as an inorganic reinforcing agent and an inorganic filling agent.

The sentence of "only calcined clay is added to butyl rubber as inorganic filler classified as an inorganic reinforcing agent and an inorganic filling agent." can be changed to "The chlorinated butyl rubber does not contain inorganic filler classified as an inorganic reinforcing agent and an inorganic filling agent other than calcined clay". The inorganic filler classified as the inorganic reinforcing agent and the inorganic filling agent indicates silica, basic magnesium carbonate, magnesium silicate, calcium carbonate, clay, talc, wollastonite, zeolite, bituminous fine powder, diatomaceous earth, silica sand, pumice powder, slate powder, alumina white, aluminum sulfate, barium sulfate, lithopone, calcium sulfate, and molybdenum disulfide. Zinc oxide, magnesium oxide, zinc carbonate, and calcium hydroxide which are vulcanization accelerators and activators are not included in this category. Titanium oxide and carbon black which are colorants are not included in this category either.

Figure 2:
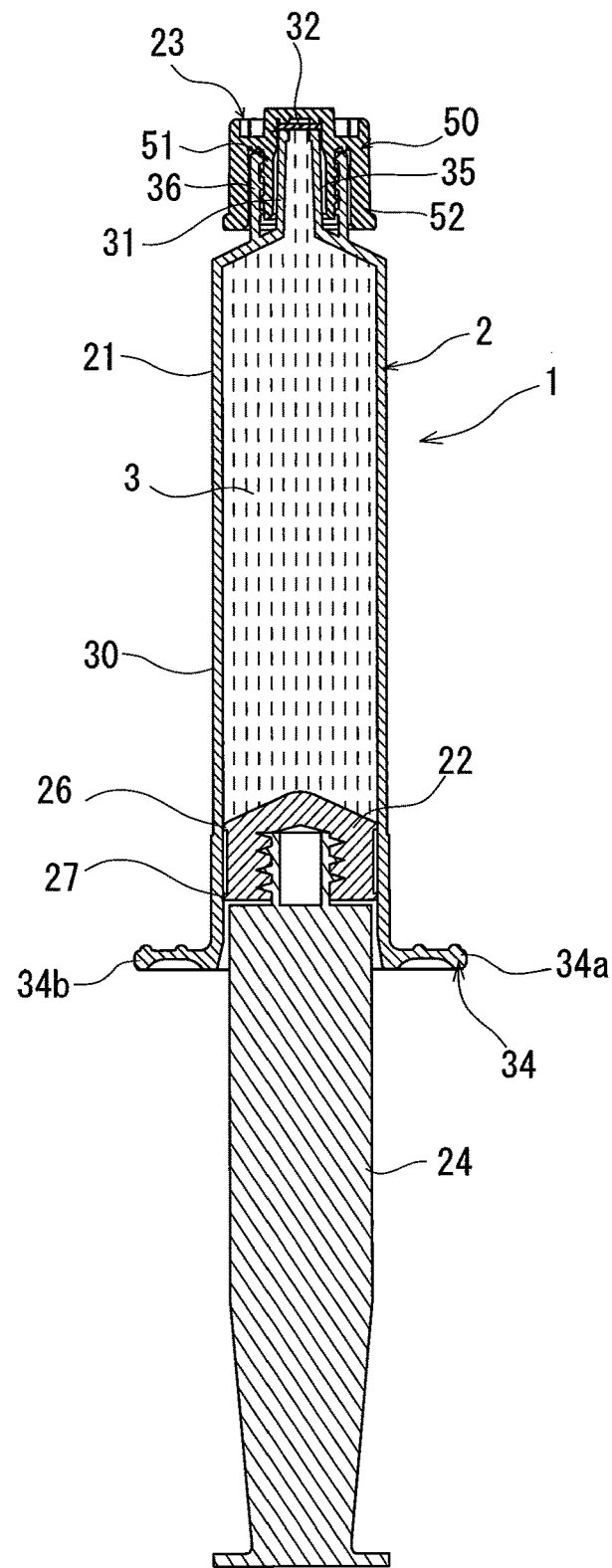
FIG. 2 is a sectional view of the prefilled syringe shown in FIG. 1.

As shown in FIG. 2, the prefilled syringe 1 of the present invention comprises the syringe 2 and the rocuronium bromide injection solution 3 filled inside the syringe 2.

As shown in FIG. 1, the syringe 2 comprises the outer cylinder 21, the gasket 22 slidably accommodated inside the outer cylinder, and the seal cap (seal member) 23 mounted on a needle mounting part 31 of the outer cylinder 21 to liquid-tightly seal the distal end opening of the outer cylinder, and a plunger 24 mounted on the gasket 22.

The rocuronium bromide injection solution 3 is accommodated inside a space constructed of the outer cylinder 21, the gasket 22, and a seal member 32 accommodated inside the seal member 23.

The outer cylinder 21 has an outer cylinder body part 30, a needle mounting part 31 formed at a distal end portion of the outer cylinder body part 30, and a flange part 34 formed at a rear end portion of the outer cylinder body part 30. The outer cylinder 21 is transparent or semitransparent. The outer cylinder body part 30 is a substantially tubular part accommodating the gasket 22 liquid-tightly and slidably. The diameter of the distal end portion (shoulder portion) of the outer cylinder body part 30 decreases in a tapered configuration toward the needle mounting part 31.

Figure 3:
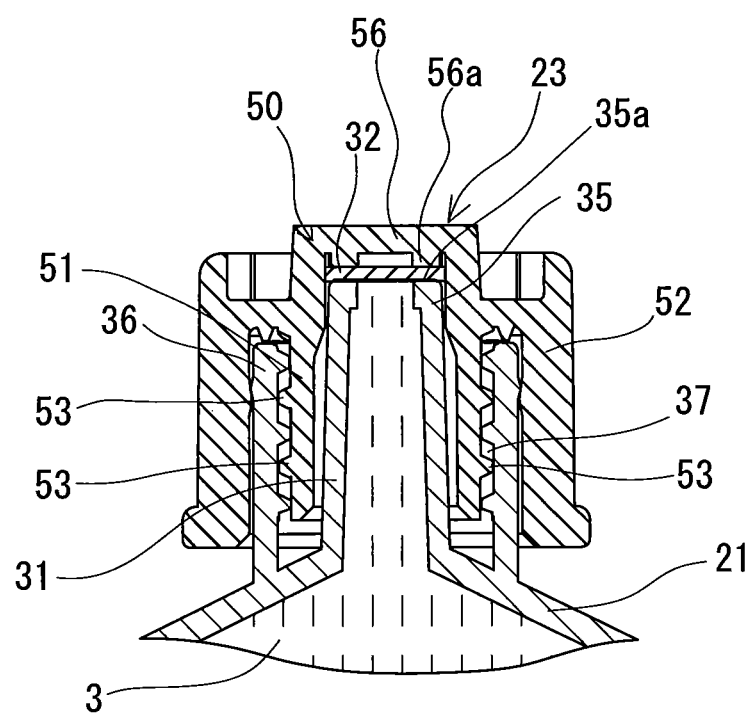
FIG. 3 is enlarged sectional view of a front part of the prefilled syringe shown in FIG. 1.

As shown in FIGS. 2 and 3, the needle mounting part 31 has a nozzle portion 35 and a collar portion 36. As shown in FIG. 2, the nozzle portion 35 is formed as a needle-mounting tip portion decreasing in its diameter toward its distal end. The nozzle portion 35 is formed at the distal end of the outer cylinder 21 and has an opening for discharging a liquid medicine filled inside the outer cylinder at its distal end. The diameter of the nozzle portion decreases in a tapered configuration toward its distal end.

A spiral groove portion 37 engageable with a spiral projected portion 53 formed on an outer circumferential surface of a nozzle portion accommodation part of the seal cap 23 is formed on an inner circumferential surface of the collar portion. As shown in FIGS. 1 and 2, the flange part 34 is an elliptic donut-shaped disk part projected vertically to the outer cylinder 21 from the entire circumference of the rear end thereof. As shown in FIGS. 1 and 2, the flange part 34 has two opposed gripping portions 34a, 34b having a wide width.

As the material for forming the outer cylinder 21, it is possible to list various resins such as polypropylene, polyethylene, polystyrene, polyamide, polycarbonate, polyvinyl chloride, poly-(4-methylpentene-1), acrylic resin, an acrylonitrile-butadiene-styrene copolymer, polyester including polyethylene terephthalate; and cyclic polyolefins. Of these resins, the polypropylene and the cyclic polyolefins are preferable because these resins are easily moldable and heat-resistant.

As shown in FIGS. 1 and 2, the gasket 22 has a body part extended substantially equally in its outer diameter and a plurality of annular ribs 26, 27 (in this embodiment, two annular ribs are formed, but not less than two annular ribs may be formed, provided that the annular ribs satisfy liquid tightness and slidability) formed on the body part of the gasket. The annular ribs 26, 27 liquid-tightly contact an inner surface of the outer cylinder 21. A distal end surface of the gasket 22 has a configuration corresponding to that of the inner surface of the distal end of the outer cylinder 21 so as to prevent a gap from being formed as much as possible between the distal end surface of the gasket and the inner surface of the distal end of the outer cylinder 21 when both surfaces contact each other.

The gasket 22 is formed of the chlorinated butyl rubber (Cl-IIR) containing only the calcined clay as the inorganic filler classified as the inorganic reinforcing agent and the inorganic filling agent. As the material of the gasket 22, butyl rubber is used because the butyl rubber is low in its oxygen permeability, is not outstanding in the evaporation of a content fluid, and is excellent in its steam sterilization resistance. In the present invention, the chlorinated butyl rubber is selected from among various types of butyl rubbers from the standpoint of cost, vulcanization reaction speed, vulcanization moldability, productivity, and physiochemical stability of vulcanizates. The chlorinated butyl rubber is a kind of halogenated butyl rubber. The butyl rubber is a copolymer of isobutyl and isoprene. The chlorinated butyl rubber to be used in the present invention is obtained by adding chlorine to the copolymer rubber of isobutylene and isoprene. The gasket 22 is formed by vulcanizing the chlorinated butyl rubber. In other words, the gasket 22 is formed of the vulcanized chlorinated butyl rubber. Usually the chlorinated butyl rubber is vulcanized simultaneously with a time when the chlorinated butyl rubber is molded into the shape of the gasket.

The preferable calcined clay to be added to the chlorinated butyl rubber is obtained by calcining kaolinite refined by means of elutriation. From the standpoint of dispersibility of the calcined clay in the chlorinated butyl rubber and the rubber property after vulcanization, it is preferable to set the average particle diameter of the calcined clay to not more than 1.0 μm. The material for forming the gasket is not specifically limited except that the material does not contain inorganic fillers classified as the inorganic reinforcing agent and the inorganic filling agent, but known medicines to be usually added to the chlorinated butyl rubber may be used.

It is favorable that the gasket contains 50 to 110 parts by weight of the calcined clay and especially favorable that the gasket contains 60 to 100 parts by weight of the calcined clay for 100 parts by weight of the chlorinated butyl rubber. Although JIS A hardness of the gasket is not specifically limited, JIS A hardness thereof is set to favorably 40 to 70 degrees and more favorably 50 to 65 degrees. Although the compression set of the gasket is not specifically limited, the compression set thereof is set to favorably not more than 20% and more favorably not more than 15%. The compression set is a value measured in conditions of 25% compression, 70±1 degree C., and 22 hours.

As fillers other than the calcined clay, organic fillers can be added to the chlorinated butyl rubber. It is possible to use any of organic fillers which are usually added to the chlorinated butyl rubber. It is preferable to use fine polypropylene powder, fine PTFE powder, and fine ultrahigh molecular weight polyethylene powder.

The gasket 22 has a concave portion extended inward from its rear end portion. The concave portion is female screw-shaped and engageable with a male screw portion formed on an outer surface of a projected portion formed at a distal end portion of the plunger 24. The engagement therebetween prevents the plunger 24 from separating from the gasket 22. The plunger 24 may be mounted on the gasket when the prefilled syringe is used.

The plunger 24 has the projected portion tubularly projected from a disk part formed at its distal end. A male screw portion which engages the concave portion of the gasket 22 is formed on an outer surface of the projected portion. The plunger 24 has a sectionally cross-shaped body part axially extended and a pressing disk part formed at a rear end portion thereof.

The seal cap 23 comprises a cap body part 50 and the seal member 32 accommodated inside the cap body part. As shown in FIGS. 1, 2, and 3, the cap body part 50 is formed in the shape of a cap and has a nozzle portion accommodation part 51 and a collar portion accommodation part 52. The seal member 32 is accommodated inside the nozzle portion accommodation part 51 of the cap body part 50.

The nozzle portion accommodation part 51 is a tubular part formed at a central portion of the seal cap 23. The nozzle portion accommodation part 51 is closed at one end thereof and open at the other end thereof. An inner diameter of the nozzle portion accommodation part 51 is substantially equal from its one end to its other end. At a central portion of a closed portion 56 of the nozzle portion accommodation part 51, there is formed an annular projected portion 56a projected from an inner surface of the closed portion 56 toward the open end thereof.

As shown in FIG. 3, the seal member 32 accommodated inside the cap body part 50 is pressurized between the annular projected portion 56a and a distal end 35a of the nozzle portion 35 of the outer cylinder 21. In other words, as shown in FIG. 5, the seal member 32 is pressed against the distal end 35a of the nozzle portion 35 of the outer cylinder 21 by the annular projected portion 56a of the cap body part 50. Thereby the seal member 32 liquid-tightly seals the distal end 35a of the nozzle portion 35.

On the outer circumferential surface of the nozzle portion accommodation part 51, there is formed the spiral projected portion 53 engageable with the spiral groove portion 37 formed on the inner circumferential surface of the collar portion 36 of the outer cylinder 21. Thereby the needle mounting part 31 and the seal cap 23 engage each other between the outer circumferential surface of the nozzle portion accommodation part 51 and the collar portion 36 of the outer cylinder 21. The collar portion accommodation part 52 is a tubular portion formed in such a way as to surround the nozzle portion accommodation part 51. The collar portion accommodation part 52 is closed at one end thereof and open at other end thereof. As shown in FIG. 1, an outer side surface (outer circumferential surface of the collar portion accommodation part 52) of the seal cap 23 is subjected to nicking processing in a longitudinal direction to prevent fingers from slipping when the seal cap is rotated.

As the material for forming the seal cap, it is possible to list various resins such as polypropylene, polyethylene, polystyrene, polyamide, polycarbonate, polyvinyl chloride, poly-(4-methylpentene-1), acrylic resin, an acrylonitrile-butadiene-styrene copolymer, polyester including polyethylene terephthalate; and cyclic polyolefins. Of these resins, the polypropylene and the cyclic polyolefins are preferable because these resins are easily moldable and heat-resistant.

In the prefilled syringe of this embodiment, the seal member 32 is formed in the shape of a disk. The diameter of the seal member 32 is set almost equally to or a little smaller than the inner diameter of the closed portion of the nozzle portion accommodation part 51. It is preferable that the seal member 32 is made by an elastic member to liquid-tightly seal the distal end opening.

As the material of the seal member 32, as with the gasket 22, butyl rubber is used because the butyl rubber is low in its oxygen permeability, is not outstanding in the evaporation of a content fluid, and is excellent in its steam sterilization resistance. In the present invention, the chlorinated butyl rubber is preferable from the standpoint of cost, vulcanization reaction speed, vulcanization moldability, productivity, and physiochemical stability of vulcanizates. The chlorinated butyl rubber is obtained by adding chlorine to the copolymer rubber of isobutylene and isoprene. It is possible to use the known chlorinated butyl rubber. As the material for forming the seal member 32, the materials of the gasket described previously are preferably used.

As described above, the seal member 32 is pressed against the distal end 35a of the nozzle portion 35 of the outer cylinder 21 by the annular projected portion 56a of the cap body part 50. Thereby the seal member 32 seals the distal end 35a of the nozzle portion 35 liquid-tightly, as shown in FIG. 3.

As shown in FIG. 3, the prefilled syringe 1 of the present invention accommodates the rocuronium bromide injection solution 3. The seal cap 23 is mounted on the nozzle portion 35 of the outer cylinder 21 owing to the engagement between the spiral groove portion 37 and the spiral projected portion 53. The distal end 35a of the nozzle portion 35 is pressed against the seal member 32 so that the seal member 32 seals the distal end 35a of the nozzle portion 35 liquid-tightly. In a case where the seal cap 23 directly contacts the rocuronium bromide injection solution 3 accommodated inside the prefilled syringe because the seal member 32 is not used for the seal cap, it is preferable to use the same material as that used to form the outer cylinder 21 as the material for forming the seal cap 23.

The rocuronium bromide injection solution specified by Japanese Pharmacopeia is filled inside the prefilled syringe 1 of the present invention. It is preferable to set the volume of the rocuronium bromide injection solution filled in the prefilled syringe to 2 to 10 ml.

In the rocuronium bromide injection solution to be used in the present invention, the concentration of rocuronium is set to favorably 5 mg/mL to 15 mg/mL and especially favorably 8 mg/mL to 12 mg/mL. A cushioning agent, a tonicity agent, and the like may be appropriately added to the rocuronium bromide injection solution. The pH of the rocuronium bromide injection solution is set to favorably 3 to 5 and more favorably 3.5 to 4.5 from the standpoint of the stability of the medicine. As a pH adjusting agent, it is possible to use acids or alkalis. More specifically, it is possible to use acetic acid or sodium hydroxide.

The prefilled syringe of this embodiment is subjected to autoclave sterilization with the rocuronium bromide injection solution being filled therein. The prefilled syringe in which the rocuronium bromide injection solution is filled is subjected to the autoclave sterilization by exposing the prefilled syringe at 118 degrees C. to 122 degrees C., at 0.8 to 2.0 kg/cm$^2$, and for 15 to 30 minutes.

EXAMPLES

The present invention is specifically described below with reference to examples shown below. The scope of the present invention is not limited to the description made in the examples.

Example 1

After 500 mg of rocuronium bromide, 100 mg of sodium acetate, and 160 mg of sodium chloride were melted, an aqueous solution containing the rocuronium bromide having a concentration of 10 mg/mL (pH: about 4) was obtained. The rocuronium bromide-containing aqueous solution was subjected to aseptic filtration to prepare a rocuronium bromide injection solution.

60 parts by weight of only calcined clay (calcined kaolinite refined by means of elutriation) was added to 100 parts by weight of chlorinated butyl rubber as an inorganic filler classified as an inorganic reinforcing agent and an inorganic filling agent to prepare a mixture. The mixture was molded and vulcanized to produce a gasket made of the chlorinated butyl rubber.

A syringe having a capacity of 10 mL was prepared by using an outer cylinder made of polypropylene, the above-described gasket, a seal cap made of the polypropylene, and a plunger made of the polypropylene. As a seal member disposed inside the seal cap, a plurality of seal members formed of the same material as that of the gasket was prepared.

After 5 mL of the rocuronium bromide injection solution was filled in the syringe, the syringe was subjected to high-pressure steam sterilization to produce a rocuronium bromide injection solution-filled prefilled syringe.

The rocuronium bromide injection solution-filled prefilled syringe was sealingly packaged with an oxygen scavenger (brand name: AGELESS (registered trademark) produced by Mitsubishi Gas Chemical Company, Inc.) and a laminate packaging material, having aluminum-metallized polyethylene terephthalate, which has gas barrier and light shielding properties. The obtained rocuronium bromide injection solution-filled prefilled syringe was set as the example 1.

Example 2

Except that 100 parts by weight of the calcined clay was added to 100 parts by weight of the chlorinated butyl rubber as the material for forming the gasket, the rocuronium bromide injection solution-filled prefilled syringe was obtained in a manner similar to that of the example 1. The rocuronium bromide injection solution-filled prefilled syringe was set as the example 2.

Comparison Example 1

60 parts by weight of only calcium carbonate treated with lignin was added to 100 parts by weight of the chlorinated butyl rubber as the inorganic filler classified as the inorganic reinforcing agent and the inorganic filling agent to prepare a mixture. The mixture was molded and vulcanized to produce a gasket made of the chlorinated butyl rubber. Except that the above-described substances were used to produce the gasket, the rocuronium bromide injection solution-filled prefilled syringe was obtained in a manner similar to that of the example 1. The obtained rocuronium bromide injection solution-filled prefilled syringe was set as the comparison example 1.

Comparison Example 2

60 parts by weight of only talc was added to 100 parts by weight of the chlorinated butyl rubber as the inorganic filler classified as the inorganic reinforcing agent and the inorganic filling agent to prepare a mixture. The mixture was molded and vulcanized to produce a gasket made of the chlorinated butyl rubber. Except that the above-described substances were used to produce the gasket, the rocuronium bromide injection solution-filled prefilled syringe was obtained in a manner similar to that of the example 1. The obtained rocuronium bromide injection solution-filled prefilled syringe was set as the comparison example 2.

Comparison Example 3

60 parts by weight of only wet silica was added to 100 parts by weight of the chlorinated butyl rubber as the inorganic filler classified as the inorganic reinforcing agent and the inorganic filling agent to prepare a mixture. The mixture was molded and vulcanized to produce a gasket made of the chlorinated butyl rubber. Except that the above-described substances were used to produce the gasket, the rocuronium bromide injection solution-filled prefilled syringe was obtained in a manner similar to that of the example 1. The obtained rocuronium bromide injection solution-filled prefilled syringe was set as the comparison example 3.

Comparison Example 4

60 parts by weight of only quarts powder was added to 100 parts by weight of the chlorinated butyl rubber as the inorganic filler classified as the inorganic reinforcing agent and the inorganic filling agent to prepare a mixture. The mixture was molded and vulcanized to produce a gasket made of the chlorinated butyl rubber. Except that the above-described substances were used to produce the gasket, the rocuronium bromide injection solution-filled prefilled syringe was obtained in a manner similar to that of the example 1. The obtained rocuronium bromide injection solution-filled prefilled syringe was set as the comparison example 4.

Comparison Example 5

As the inorganic filler classified as the inorganic reinforcing agent and the inorganic filling agent, 55 parts by weight of the calcined clay and 5 parts by weight of the wet silica were added to 100 parts by weight of the chlorinated butyl rubber to prepare a mixture. The mixture was molded and vulcanized to produce a gasket made of the chlorinated butyl rubber. Except that the above-described substances were used to produce the gasket, the rocuronium bromide injection solution-filled prefilled syringe was obtained in a manner similar to that of the example 1. The obtained rocuronium bromide injection solution-filled prefilled syringe was set as the comparison example 5.

Experiment 1

Surface Observation

Each of the rocuronium bromide injection formulations, to be filled in prefilled syringes, which were obtained in the examples 1 and 2 and the comparison examples 1 through 5 was preserved at 60 degrees C. (humidity: without artificial control). The surface states of gaskets were observed visually and under a microscope when the test started and after the lapse of one week from the start of the test. Results were as shown in table 1.

TABLE 1

|  | 60 degrees C. | | |
|---|---|---|---|
|  | Test start time (after sterilization) | One week | |
|  |  | Checked visually | Checked under microscope |
| Example 1 | Non-denatured | Undeformed | Undeformed |
| Example 2 | Non-denatured | Undeformed | Undeformed |
| Comparison example 1 | Non-denatured | Denatured | Denatured |
| Comparison example 2 | Non-denatured | Undeformed | Finely denatured |
| Comparison example 3 | Non-denatured | Undeformed | Finely denatured |
| Comparison example 4 | Non-denatured | Undeformed | Finely denatured |
| Comparison example 5 | Non-denatured | Undeformed | Finely denatured |

Experiment 2

Stability Test

Each three rocuronium bromide injection solution-filled prefilled syringes obtained in the examples 1 and 2 and the comparison examples 1 through 5 were preserved at 60 degrees C. (humidity: without artificial control). The survival rate (%) of each rocuronium bromide was measured by a high-performance liquid chromatography when the test started and after the lapse of one week from the start of the test (the values shown in table 2 are average values in n=3). Results were as shown in table 2.

(1) Method of Measuring Survival Rate

After 2 mL of the injection solution was collected from each rocuronium bromide injection solution-filled prefilled syringe, acetonitrile/water mixture (9:1) was added to each injection solution to obtain specimen solutions each having a volume of 20 mL. About 50 mg of a standard product of the rocuronium bromide accurately measured was dissolved in the acetonitrile/water mixture (9:1), standard solutions each having a volume 50 mL were obtained. Tests were conducted on the specimen solutions and the standard solutions each having a volume of 5 μL by using liquid chromatography in the following conditions. A peak area of rocuronium of each solution was found.

(2) Test Conditions

Detector: an ultraviolet absorption meter (measurement wavelength: 210 nm)

Column: 5 μm of silica gel for use in liquid chromatography was filled in a stainless tube having an inner diameter of 4.6 mm and a length of 25 cm.

Temperature of column: a constant temperature in the vicinity of 30 degrees C.

Mobile phase: 4.53 g/L of a tetramethylammonium hydroxide pentahydrate solution whose pH was adjusted to 7.4 by phosphoric acid/acetonitrile (10:90)

TABLE 2

|  | 60 degrees C. | |
|---|---|---|
|  | Test start time (after sterilization) | One week |
| Example 1 | 100% | 99.0% |
| Example 2 | 100% | 100.2% |
| Comparison example 1 | 100% | 99.8% |
| Comparison example 2 | 100% | 99.1% |
| Comparison example 3 | 100% | 99.1% |
| Comparison example 4 | 100% | 99.5% |
| Comparison example 5 | 100% | 99.5% |

INDUSTRIAL APPLICABILITY

The rocuronium bromide injection solution-filled prefilled syringe of the present invention is as described below.

(1) A rocuronium bromide injection solution-prefilled syringe comprises a syringe having an outer cylinder made of synthetic resin, a gasket which is accommodated inside said outer cylinder and liquid-tightly slidable inside said outer cylinder, and a seal member for sealing a distal end opening of said outer cylinder; and a rocuronium bromide injection solution filled inside said syringe, wherein said gasket is formed by vulcanized chlorinated butyl rubber added calcined clay, and said calcined clay is only added as an inorganic filler classified as an inorganic reinforcing agent and an inorganic filling agent.

The gasket is formed by adding only calcined clay to chlorinated butyl rubber as an inorganic filler classified as an inorganic reinforcing agent and an inorganic filling agent and vulcanizing the chlorinated butyl rubber. Thereby even though the gasket is in contact with an acidic solution containing the rocuronium bromide for a long time, the gasket is not deformed or denatured.

Therefore it is possible to preserve the rocuronium bromide injection solution-filled prefilled syringe for a long time.

The above-described embodiments may be as described below.

(2) A rocuronium bromide injection solution-prefilled syringe according to the above (1), wherein said gasket is added 50 to 110 parts by weight of said calcined clay per 100 parts by weight of said chlorinated butyl rubber.

(3) A rocuronium bromide injection solution-prefilled syringe according to the above (1) or (2), wherein an average particle diameter of said calcined clay is set to not more than 1.0 μm.

(4) A rocuronium bromide injection solution-prefilled syringe according to any one of the above (1) through (3), wherein said synthetic resin is polypropylene or cyclic polyolefin.

(5) A rocuronium bromide injection solution-prefilled syringe according to any one of the above (1) through (4), wherein said prefilled syringe is subjected to high-pressure steam sterilization.

The invention claimed is:

1. A rocuronium bromide injection solution-prefilled syringe comprises a syringe having an outer cylinder made of synthetic resin, a gasket which is accommodated inside said outer cylinder and liquid-tightly slidable inside said outer cylinder, a seal member sealing a distal end opening of said outer cylinder; and a rocuronium bromide injection solution filled inside said syringe, wherein said gasket is formed by vulcanized chlorinated butyl rubber to which is only added calcined clay as an inorganic filler and an average particle diameter of said calcined clay is not more than 1.0 μm.

2. A rocuronium bromide injection solution-prefilled syringe according to claim 1, wherein said gasket comprises 50 to 110 parts by weight of said calcined clay per 100 parts by weight of said chlorinated butyl rubber.

3. A rocuronium bromide injection solution-prefilled syringe according to claim 1, wherein said synthetic resin is polypropylene or cyclic polyolefin.

4. A rocuronium bromide injection solution-prefilled syringe according to claim 1, wherein said prefilled syringe is subjected to high-pressure steam sterilization.

5. A rocuronium bromide injection solution-prefilled syringe according to claim 1, wherein said calcined clay is a calcined kaolinite refined by elutriation.

6. A rocuronium bromide injection solution-prefilled syringe according to claim 1, wherein said gasket and said seal member contains 50 to 110 parts by weight of said calcined clay per 100 parts by weight of said chlorinated butyl rubber.

7. A rocuronium bromide injection solution-prefilled syringe comprising:
a syringe having an outer cylinder made of synthetic resin, a gasket accommodated inside said outer cylinder and liquid-tightly slidable inside said outer cylinder, a seal cap and a rocuronium bromide injection solution filled inside said syringe;
said seal cap comprising a cap body part and a seal member sealing a distal end opening of said outer cylinder;
said gasket being formed by vulcanized chlorinated butyl rubber to which is added calcined clay, and said calcined clay is only added as an inorganic filler classified as an inorganic reinforcing agent and an inorganic filling agent, said gasket does not contain inorganic filler classified as an inorganic reinforcing agent and an inorganic filling agent other than said calcined clay, and an average particle diameter of said calcined clay is not more than 1.0 μmm; and
said seal member being formed of vulcanized chlorinated butyl rubber to which is added calcined clay, and said calcined clay is only added as an inorganic filler classified as an inorganic reinforcing agent and an inorganic filling agent, said seal member does not contain inorganic filler classified as an inorganic reinforcing agent and an inorganic filling agent other than said calcined clay, and an average particle diameter of said calcined clay in said vulcanized chlorinated butyl rubber of said seal member is not more than 1.0 μm.

8. A rocuronium bromide injection solution-prefilled syringe according to claim 7, wherein said calcined clay is a calcined kaolinite refined by elutriation.

* * * * *